United States Patent
Hickey et al.

(10) Patent No.: US 8,436,029 B2
(45) Date of Patent: May 7, 2013

(54) PHARMACEUTICAL FORMS, AND METHODS OF MAKING AND USING THE SAME

(75) Inventors: Magali Bourghol Hickey, Medford, MA (US); Matthew L. Peterson, Hopkinton, MA (US); Örn Almarsson, Shrewsbury, MA (US); Michael J. Zaworotko, Tampa, FL (US); Tanise Shattock, Montville, NJ (US); Julius F. Remenar, Framingham, MA (US); Mark Tawa, Acton, MA (US)

(73) Assignees: Transform Pharmaceuticals, Inc., Lexington, MA (US); University of South Florida, Tampa, FL (US)

( * ) Notice: Subject to any disclaimer, the term of this patent is extended or adjusted under 35 U.S.C. 154(b) by 1326 days.

(21) Appl. No.: 10/599,010

(22) PCT Filed: Mar. 17, 2005

(86) PCT No.: PCT/US2005/009305
§ 371 (c)(1),
(2), (4) Date: Jul. 29, 2011

(87) PCT Pub. No.: WO2005/089511
PCT Pub. Date: Sep. 29, 2005

(65) Prior Publication Data
US 2012/0015993 A1  Jan. 19, 2012

Related U.S. Application Data

(60) Provisional application No. 60/554,834, filed on Mar. 19, 2004, provisional application No. 60/566,647, filed on Apr. 30, 2004, provisional application No. 60/610,296, filed on Sep. 16, 2004, provisional application No. 60/637,907, filed on Dec. 21, 2004.

(51) Int. Cl.
*A01N 43/64* (2006.01)
*A61K 31/41* (2006.01)
*C07D 473/00* (2006.01)

(52) U.S. Cl.
USPC .................................. 514/383; 544/267.4

(58) Field of Classification Search .................. 424/400
See application file for complete search history.

(56) References Cited

FOREIGN PATENT DOCUMENTS

WO  WO 03/053920 A1   7/2003
WO  WO 03053438 A1 *  7/2003

OTHER PUBLICATIONS

"ARIMIDEX® (anastrozole)" [Retrieved Dec. 5, 2012]. Retrieved from the internet <URL: http://www.accessdata.fda.gov/drugsatfda_docs/label/2011/020541s026lbl.pdf>.*
Encyclopedia, Wikipedia—free encyclopedia from Internet, p. 1-2 (2006).
PCT International Search Report, dated Sep. 20, 2006, for PCT Int'l. Appln. No. PCT/US05/09305.

* cited by examiner

*Primary Examiner* — Robert T Crow
*Assistant Examiner* — Doan Phan
(74) *Attorney, Agent, or Firm* — Saliwanchik, Lloyd & Eisenschenk

(57) ABSTRACT

Crystalline salts, polymorphs, solvates, and hydrates of bicalutamide, 5-fluorouracil, donepezil, anastrozole, nelfinavir, mirtazapine, lansoprazole, and tamsulosin, or derivatives thereof are provided by the subject invention. Methods of making and using the same are also provided.

7 Claims, 17 Drawing Sheets

PHARMACEUTICAL FORMS, AND METHODS OF MAKING AND USING THE SAME

FIELD OF THE INVENTION

The present invention relates to drug-containing compositions, pharmaceutical compositions comprising such drugs, and methods for preparing and using the same.

BACKGROUND OF THE INVENTION

Drugs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different solvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

It would be advantageous to have new forms of bicalutamide, donepezil, anastrozole, nelfinavir, mirtazapine, lansoprazole, 5-fluorouracil, and/or tamsulosin that have improved properties, in particular, as oral formulations. Specifically, it is desirable to identify improved forms of the drug that exhibit significantly increased aqueous solubilities, stability, hygroscopicity and decreased form polymorphism. It is also desirable to increase the dissolution rate of drug-containing pharmaceutical compositions in water, increase the bioavailability of orally-administered compositions, and provide a more rapid onset to therapeutic effect. It is also desirable to have a form of the drug which, when administered to a subject, reaches a peak plasma level faster and/or has a longer lasting plasma concentration and higher overall exposure at high doses when compared to equivalent amounts of the drug in its presently-known form.

SUMMARY OF THE INVENTION

It has now been found that new salt forms, polymorphs, solvates, and hydrates of active pharmaceutical ingredients (API) selected from the group of APIs consisting of bicalutamide, 5-fluorouracil, donepezil, anastrozole, nelfinavir, mirtazapine, lansoprazole, and tamsulosin can be obtained which have different properties as compared to the converted forms of the parent API.

Accordingly, in a first aspect, the present invention provides a bicalutamide, donepezil, anastrozole, nelfinavir, or tamsulosin salt made by reacting bicalutamide, donepezil, anastrozole, nelfinavir, or tamsulosin with an organic or inorganic acid in a crystallization solvent, wherein the form has an aqueous solubility of approximately 5 micrograms/mL to approximately 100 mg/mL.

When a salt of bicalutamide, donepezil, anastrozole, nelfinavir, tamsulosin, or a derivative thereof is desired, salt forming components will generally be used in stoichiometric quantities. Salt forming components of the subject invention include, and are not limited to compounds containing: chloride, bromide, iodide, acetate, salicylate, benzenesulfonate, benzoate, bicarbonate, bitartrate, calcium edetate, camsylate, carbonate, citrate, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, oxalate, panthothenate, phosphate/diphosphate, polygalacturonate, salicylate, stearate, succinate, sulfate, tannate, tartrate, teoclate, triethiodide, amino acids, pamoate (i.e., 1,1'-methylene-bis-(2-hydroxy-3-naphthoate)), alkali metal or alkaline earth metals (e.g., calcium, magnesium, sodium, lithium, zinc, potassium, or iron), or basic organic compounds (such as amines, for example N-methylglucamine and TRIS (trishydroxymethyl aminomethane).

The amount of salt forming component used to make salts of bicalutamide, donepezil, anastrozole, nelfinavir, or tamsulosin is typically about 0.5-1 equivalents of salt forming component for each equivalent of bicalutamide, donepezil, anastrozole, nelfinavir, or tamsulosin. These mole ratios are found when a bicalutamide, donepezil, anastrozole, nelfinavir, or tamsulosin salt is prepared according to methods described herein. Other mole ratios can also be used in various methods. The physical form of the salt is preferably compatible with its ability to be formed as a pharmaceutical composition readily. It is preferred that the salt is in a crystalline form and such crystalline forms are readily preparable according to the methods described herein.

The invention further provides a pharmaceutical composition comprising a salt of bicalutamide, donepezil, anastrozole, nelfinavir, or tamsulosin. Typically, the pharmaceutical composition further comprises one or more pharmaceutically-acceptable carriers, diluents or excipients. Pharmaceutical compositions according to the invention are described in further detail below.

In a further aspect, the present invention provides a process for the preparation of a salt of bicalutamide, donepezil, anastrozole, nelfinavir, or tamsulosin, which comprises:

(1) mixing of bicalutamide, donepezil, anastrozole, nelfinavir, tamsulosin, or a derivative thereof with a salt forming component to form a mixture;

(2) subjecting the mixture to conditions which salify bicalutamide, donepezil, anastrozole, nelfinavir, tamsulosin, or a derivative thereof whereby crystals of a of bicalutamide, donepezil, anastrozole, nelfinavir, or tamsulosin salt are formed; and (3) optionally isolating the salt.

In one embodiment, the bicalutamide, donepezil, anastrozole, nelfinavir, tamsulosin, or a derivative thereof may be mixed with salt forming components in solution. Any suitable solvent may be used for this step, including organic solvents or mixed solvents. Solvents comprising alcohols are a good example with methanol a preferred alcohol. A water/methanol mixed solvent is also a possibility.

Any conditions which salify the bicalutamide, donepezil, anastrozole, nelfinavir, tamsulosin, or a derivative thereof from solution may be used whereby crystals of bicalutamide, donepezil, anastrozole, nelfinavir, or tamsulosin salt are formed. Conveniently, this step includes evaporation of the solvent so as to concentrate the solute whereby bicalutamide, donepezil, anastrozole, nelfinavir, or tamsulosin salt crystals may be precipitated. In a preferred embodiment, the solution is first heated to ensure mixing and salt formation, followed by cooling so as to enable salt crystals to precipitate.

In an alternative embodiment, the bicalutamide, donepezil, anastrozole, nelfinavir, tamsulosin, or a derivative thereof is mixed with the salt forming component in a solid phase. Any suitable means for mixing may be used in this step, including commercially-available solid mixers. The solid mixture thus formed is preferably heated so as to cause salification of the bicalutamide, donepezil, anastrozole, nelfinavir, tamsulosin, or a derivative thereof with a salt forming component. In this step it is possible that salt crystals may form spontaneously upon heating. It is preferred in this embodiment to ensure that the solid mixture is comminuted, typically by grinding the mixture prior to heating so as to facilitate salification.

The salt, typically in the form of crystals, may be isolated by any conventional technique.

In a further aspect, the present invention provides a process for modulating the solubility of bicalutamide, donepezil, anastrozole, nelfinavir, tamsulosin, or a derivative thereof for use in a pharmaceutical composition, which process comprises:
(1) mixing of bicalutamide, donepezil, anastrozole, nelfinavir, tamsulosin, or a derivative thereof with a salt forming component to form a mixture; and
(2) salifying the bicalutamide, donepezil, anastrozole, nelfinavir, tamsulosin, or a derivative thereof with the salt forming component so that the solubility of the bicalutamide, donepezil, anastrozole, nelfinavir, tamsulosin, or a derivative thereof is modulated.

In a further aspect, the present invention provides a process for modulating the dose response of bicalutamide, donepezil, anastrozole, nelfinavir, tamsulosin, or a derivative thereof for use in a pharmaceutical composition, which process comprises:
(1) mixing of bicalutamide, donepezil, anastrozole, nelfinavir, tamsulosin, or a derivative thereof with a salt forming component to form a mixture, and
(2) salifying the bicalutamide, donepezil, anastrozole, nelfinavir, tamsulosin, or a derivative thereof with the salt forming component so that the dose response of the bicalutamide, donepezil, anastrozole, nelfinavir, tamsulosin, or a derivative thereof is modulated.

The processes according to the present invention may each comprise a further step or steps in which the bicalutamide, donepezil, anastrozole, nelfinavir, or tamsulosin salt produced thereby is incorporated into a pharmaceutical composition.

In another aspect, the present invention provides novel polymorphs of bicalutamide, 5-fluorouracil, donepezil, anastrozole, nelfinavir, tamsulosin, or a derivative thereof.

In another embodiment, a bicalutamide, 5-fluorouracil, donepezil, anastrozole, nelfinavir, or tamsulosin polymorph is formed by the crystallization of bicalutamide, 5-fluorouracil, donepezil, anastrozole, nelfinavir, or tamsulosin in an appropriate solvent, wherein the polymorph has an aqueous solubility of at least about 100 micrograms/mL.

In another aspect, the present invention provides a process for the preparation of a novel polymorph of bicalutamide, 5-fluorouracil, donepezil, anastrozole, nelfinavir, tamsulosin, or a derivative thereof which comprises:
(a) mixing bicalutamide, 5-fluorouracil, donepezil, anastrozole, nelfinavir, tamsulosin, or a derivative thereof with an appropriate solvent; and
(b) crystallizing the polymorph of bicalutamide, 5-fluorouracil, donepezil, anastrozole, nelfinavir, tamsulosin, or a derivative thereof under conditions which lead to the formation of the polymorph.

In another aspect, the present invention provides novel hydrates of bicalutamide, 5-fluorouracil, donepezil, anastrozole, nelfinavir, mirtazapine, lansoprazole, tamsulosin, celecoxib sodium salt or a derivative thereof.

In another embodiment, a bicalutamide, 5-fluorouracil, donepezil, anastrozole, nelfinavir, mirtazapine, lansoprazole, or tamsulosin hydrate is formed by the crystallization of bicalutamide, 5-fluorouracil, donepezil, anastrozole, nelfinavir, or tamsulosin in an appropriate solvent, wherein the hydrate has an aqueous solubility of at least about 100 micrograms/mL.

In another aspect, the present invention provides a process for the preparation of a novel hydrate of bicalutamide, 5-fluorouracil, donepezil, anastrozole, nelfinavir, mirtazapine, lansoprazole, tamsulosin, or a derivative thereof which comprises:
(a) mixing bicalutamide, 5-fluorouracil, donepezil, anastrozole, nelfinavir, mirtazapine, lansoprazole, tamsulosin, or a derivative thereof with an appropriate solvent and/or water; and
(b) crystallizing the hydrate of bicalutamide, 5-fluorouracil, donepezil, anastrozole, nelfinavir, mirtazapine, lansoprazole, tamsulosin, or a derivative thereof under conditions which lead to the formation of the hydrate.

In another embodiment, a bicalutamide, 5-fluorouracil, donepezil, anastrozole, nelfinavir, mirtazapine, lansoprazole, fluconazole, or tamsulosin solvate is formed by the crystallization of bicalutamide, 5-fluorouracil, donepezil, anastrozole, nelfinavir, mirtazapine, lansoprazole, fluconazole, or tamsulosin in an appropriate solvent, wherein the solvate has an aqueous solubility of at least about 100 micrograms/mL.

In another aspect, the present invention provides a process for the preparation of a novel solvate of bicalutamide, 5-fluorouracil, donepezil, anastrozole, nelfinavir, mirtazapine, lansoprazole, fluconazole, tamsulosin, or a derivative thereof which comprises:
(a) mixing bicalutamide, 5-fluorouracil, donepezil, anastrozole, nelfinavir, mirtazapine, lansoprazole, fluconazole, tamsulosin, or a derivative thereof with an appropriate solvent and/or water; and
(b) crystallizing the hydrate of bicalutamide, 5-fluorouracil, donepezil, anastrozole, nelfinavir, mirtazapine, lansoprazole, fluconazole, tamsulosin, or a derivative thereof under conditions which lead to the formation of the solvate.

In a still further aspect of the invention, a method is provided for treating a subject, preferably a human subject, with an illness selected from the group consisting of Alzheimer's Disease, prostate cancer, benign prostate cancer, breast cancer, cancer, HIV infection, duodenal or gastric ulcers, major depressive disorder, candidiasis, meningitis, and diabetes where bicalutamide, 5-fluorouracil, donepezil, anastrozole, nelfinavir, mirtazapine, lansoprazole, or tamsulosin is an effective active pharmaceutical for said illness. The method comprises administering to the subject a therapeutically-effective amount of a salt or a polymorph of bicalutamide, 5-fluorouracil, donepezil, anastrozole, nelfinavir, mirtazapine, lansoprazole, or tamsulosin or a derivative thereof.

The invention further provides a medicament comprising a salt of bicalutamide, donepezil, anastrozole, nelfinavir, or tamsulosin. Typically, the medicament further comprises one or more pharmaceutically-acceptable carriers, diluents or excipients. Medicaments according to the invention are described in further detail below.

In a further aspect, the present invention provides a process for modulating the solubility of bicalutamide, donepezil, anastrozole, nelfinavir, tamsulosin, or a derivative thereof for use in a medicament, which process comprises:
(1) mixing of bicalutamide, donepezil, anastrozole, nelfinavir, tamsulosin, or a derivative thereof with a salt forming component to form a mixture; and
(2) salifying the bicalutamide, donepezil, anastrozole, nelfinavir, tamsulosin, or a derivative thereof with the salt forming component so that the solubility of the bicalutamide, donepezil, anastrozole, nelfinavir, tamsulosin, or a derivative thereof is modulated.

In a further aspect, the present invention provides a process for modulating the dose response of bicalutamide, donepezil, anastrozole, nelfinavir, tamsulosin, or a derivative thereof for use in a medicament, which process comprises:

(1) mixing of bicalutamide, donepezil, anastrozole, nelfinavir, tamsulosin, or a derivative thereof with a salt forming component to form a mixture, and (2) salifying the bicalutamide, donepezil, anastrozole, nelfinavir, tamsulosin, or a derivative thereof with the salt forming component so that the dose response of the bicalutamide, donepezil, anastrozole, nelfinavir, tamsulosin, or a derivative thereof is modulated.

The processes according to the present invention may each comprise a further step or steps in which the bicalutamide, 5-fluorouracil, donepezil, anastrozole, nelfinavir, mirtazapine, lansoprazole, celecoxib sodium, or tamsulosin salt, polymorph, or hydrate produced thereby is incorporated into a medicament.

DETAILED DESCRIPTION OF THE INVENTION

Figure 1:
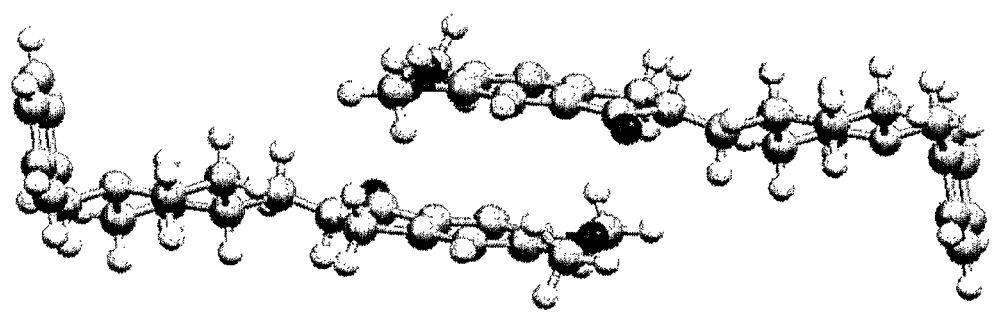
FIG. 1 shows the pi stacking of donepezil free base, Form III

Pharmaceutically acceptable salts, hydrates, solvates, and polymorphs of bicalutamide, 5-fluorouracil, donepezil, anastrozole, nelfinavir, mirtazapine, lansoprazole, fluconazole, celecoxib sodium, or tamsulosin and derivatives thereof can be administered by controlled- or delayed-release means. Controlled-release pharmaceutical products and medicaments have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels; toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the bicalutamide, 5-fluorouracil, donepezil, anastrozole, nelfinavir, mirtazapine, lansoprazole, fluconazole, celecoxib sodium, or tamsulosin salts, polymorphs, and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of bicalutamide, donepezil, anastrozole, nelfinavir, or tamsulosin and thus effect controlled delivery of the drug. Examples of specific anion exchangers include, but are not limited to, Duolite® A568 and Duolite® AP143 (Rohm & Haas, Spring House, Pa. USA).

One embodiment of the invention encompasses a unit dosage form which comprises a pharmaceutically acceptable salt of bicalutamide, donepezil, anastrozole, nelfinavir, mirtazapine, lansoprazole, fluconazole, celecoxib sodium, or tamsulosin, or a polymorph, solvate, hydrate, dehydrate, co-crystal, anhydrous, or amorphous form thereof, and one or more pharmaceutically acceptable excipients or diluents, wherein the pharmaceutical composition, medicament, or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g., bicalutamide, donepezil, anastrozole, nelfinavir, or tamsulosin salt) into a hard tablet, coating the tablet with cellulose derivatives to form a semipermeable membrane, and then drilling an orifice in the coating (e.g., with a laser). (Kim, Cherng-ju, Controlled Release Dosage Form Design, 231-238 Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively deliver drugs with low water solubility. Because bicalutamide, donepezil, anastrozole, nelfinavir, or tamsulosin salts and complexes of this invention are far more soluble in water than bicalutamide, donepezil, anastrozole, nelfinavir, or tamsulosin itself, they are well suited for osmotic-based delivery to patients. This invention does, however, encompass the incorporation of bicalutamide, donepezil, anastrozole, nelfinavir, or tamsulosin, and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent to the exit orifice and in direct or indirect contacting relationship with the expandable layer; and a flow-promoting layer interposed between the inner surface of the wall and at least the external surface of the drug layer located within the cavity, wherein the drug layer comprises a salt of bicalutamide, donepezil, anastrozole, nelfinavir, or tamsulosin, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of bicalutamide, donepezil, anastrozole, nelfinavir, or tamsulosin, or a polymorph, solvate, hydrate, dehydrate, co-crystal, anhydrous, or amorphous form thereof. See U.S. Pat. No. 6,342,249, the entirety of which is incorporated herein by reference.

Excipients employed in pharmaceutical compositions of the present invention can be solids, semi-solids, liquids or combinations thereof. Preferably, excipients are solids. Compositions of the invention containing excipients can be prepared by known technique of pharmacy that comprises admixing an excipient with a drug or therapeutic agent. A pharmaceutical composition of the invention contains a desired amount of drug per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with drugs. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of drugs, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a drug of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the drug in close association with water, a condition that is believed to improve bioavailability of the composition.

Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the drug in an aqueous medium. Without being bound by theory, it is believed that the effervescent agent is effective to accelerate dispersion of the drug, from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid acids useful in the invention include citric acid, tartaric acid (as D-, L-, or D/L-tartaric acid), malic acid, maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of drugs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of drug; about 10% to about 50%, about 25% to about 50%, about 30% to about 45%, or about 30% to about 35% by weight of a an excipient which inhibits crystallization; and about 5% to about 50%, about 10% to about 40%, about 15% to about 35%, or about 30% to about 35% by weight of a binding agent. In one example, the weight ratio of the drug to the excipient which inhibits crystallization to binding agent is about 1 to 1 to 1.

Solid dosage forms of the invention can be prepared by any suitable process, not limited to processes described herein.

An illustrative process comprises (a) a step of blending a salt of the invention with one or more excipients to form a blend, and (b) a step of tableting or encapsulating the blend to form tablets or capsules, respectively.

In a preferred process, solid dosage forms are prepared by a process comprising (a) a step of blending a drug salt of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the drug is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Uses for bicalutamide, 5-fluorouracil, donepezil, anastrozole, nelfinavir, mirtazapine, lansoprazole, fluconazole, celecoxib, or tamsulosin are well known in the art and include the treatment of Alzheimer's Diseases, HIV infection, duodenal or gastric ulcers, GERD, erosive esophagitis, major depressive disorder, arthritis, rheumatoid arthritis, inflammation, diabetes, prostate cancer, benign prostate cancer, breast cancer, or other cancers. The dosage and administration for bicalutamide, 5-fluorouracil, donepezil, anastrozole, nelfinavir, mirtazapine, lansoprazole, fluconazole, celecoxib, or tamsulosin compositions of the present invention can be determined using routine methods in the art but will generally be about those dosages recommended by the package inserts (or Physician's Desk Reference) for bicalutamide, 5-fluorouracil, donepezil, anastrozole, nelfinavir, mirtazapine, lansoprazole, fluconazole, celecoxib, or tamsulosin in their unmodified (or parent drug) states.

Excipients employed in medicaments of the present invention can be solids, semi-solids, liquids or combinations thereof. Preferably, excipients are solids. Medicaments of the invention containing excipients can be prepared by known techniques of pharmacy that comprise admixing an excipient with a drug or therapeutic agent. A medicament of the invention contains a desired amount of drug per dose unit and, if intended for oral administration, can be in the form, for example, of a tablet, a caplet, a pill, a hard or soft capsule, a lozenge, a cachet, a dispensable powder, granules, a suspension, an elixir, a dispersion, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare medicaments of the invention.

Medicaments of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with drugs. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of drugs, stability, pre-compression flowability, and/or drying properties at a relatively low diluent cost. It provides a high density substrate that aids densification during granulation (where wet granulation is employed) and therefore improves blend flow properties and tablet properties.

Medicaments of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R. T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated medicaments of the present invention.

Medicaments of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a drug of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the medicament.

Many of the binding agents are polymers comprising amide, ester, ether, alcohol or ketone groups and, as such, are preferably included in medicaments of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Medicaments of the invention optionally comprise one or more pharmaceutically acceptable wetting agents as excipients. Such wetting agents are preferably selected to maintain the drug in close association with water, a condition that is believed to improve bioavailability of the composition.

Non-limiting examples of surfactants that can be used as wetting agents in medicaments of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the medicament.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the medicament.

Medicaments of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the medicament.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the medicament.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in medicaments of the present invention. Tablets can be coated, for example with an enteric coating, or uncoated. Medicaments of the invention can further comprise, for example, buffering agents.

Optionally, one or more effervescent agents can be used as disintegrants and/or to enhance organoleptic properties of medicaments of the invention. When present in medicaments of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the drug in an aqueous medium. Without being bound by theory, it is believed that the effervescent agent is effective to accelerate dispersion of the drug, from the dosage form in the gastrointestinal tract, thereby further enhancing absorption and rapid onset of therapeutic effect. When present in a medicament of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the medicament.

Medicaments of the present invention can comprise about 10% to about 50%, about 25% to about 50%, about 30% to about 45%, or about 30% to about 35% by weight of drug; about 10% to about 50%, about 25% to about 50%, about 30% to about 45%, or about 30% to about 35% by weight of a an excipient which inhibits crystallization; and about 5% to about 50%, about 10% to about 40%, about 15% to about 35%, or about 30% to about 35% by weight of a binding agent. In one example, the weight ratio of the drug to the excipient which inhibits crystallization to binding agent is about 1 to 1 to 1.

EXAMPLES

Analytical Methods

Differential scanning calorimetric (DSC) analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E; Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the samples were performed by placing the bicalutamide, 5-fluorouracil, donepezil, anastrozole, nelfinavir, mirtazapine, lansoprazole, fluconazole, celecoxib, or tamsulosin sample or a derivative thereof in an aluminum pan with a crimped pan closure. The starting temperature was typically 20 degrees C. with a heating rate of 10 degrees C./minute, and the ending temperature was 250 degrees C.

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E; Build 3.1.0.40 (2001 TA Instruments-Water LLC).

For the TGA experiments, the purge gas used was dry nitrogen, the balance purge was 40 mL/minute $N_2$, and the sample purge was 60 mL/minute $N_2$.

TGA was performed on the sample by placing the bicalutamide, 5-fluorouracil, donepezil, anastrozole, nelfinavir, mirtazapine, lansoprazole, fluconazole, celecoxib, or tamsulosin derivative or salt sample in a platinum pan. The starting temperature was typically 20 degrees C. with a heating rate of 10 degrees C./minute, and the ending temperature was 300 degrees C.

A powder X-ray diffraction (PXRD) pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995-2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0-5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2-60 degrees; the integration chi range was 0-360 degrees; the number of chi segments was 1; the step size used was 0.02; the integration utility was cylint; normalization was used; dark counts were 8; omega offset was 180; and chi and phi offsets were 0.

Single crystal x-ray crystallographic analyses conducted in connection with the experiments described herein were used to determine unit cell dimensions, space group, and atomic position of all atoms in a compound relative to the origin of its unit cell. The unit cell dimension is defined by three parameters; length of the sides of the cell, relative angles of sides to each other and the volume of the cell. The lengths of the sides of the unit cell are defined by a, b and c. The relative angles of the cell sides are defined by alpha, beta, and gamma. The volume of the cell is defined as V. A more detailed account of unit cells can be found in Chapter 3 of Stout. & Jensen, X-Ray Structure Determination; A Practical Guide, Mac Millian Co., New York, N.Y. (1968).

The results of a single crystal x-ray analysis are limited to the crystal placed in the x-ray beam. Crystallographic data on a large group of crystals provides powder x-ray diffraction. If the powder is a pure crystalline compound a simple powder diagram is obtained. To compare the results of a single crystal analysis and powder x-ray analysis a simple calculation can be done converting the single crystal data into a powder x-ray diagram, SHELXTL Plus® computer program, Reference Manual by Siemens Analytical X-ray Instrument, Chapter 10, p. 179-181, 1990. This conversion is possible because the single crystal experiment routinely determines the unit cell dimensions, space group, and atomic positions. These parameters provide a basis to calculate a perfect powder pattern. Comparing this calculated powder pattern and the powder pattern experimentally obtained from a large collection of crystals will confirm if the results of the two techniques are the same.

Single crystal x-ray data were collected on a Bruker SMART-APEX CCD diffractometer (M. J. Zaworotko, Department of Chemistry, University of South Florida). Lattice parameters were determined from least squares analysis. Reflection data was integrated using the program SAINT. The structure was solved by direct methods and refined by full matrix least squares using the program SHELXTL (Sheldrick, G. M. SHELXTL, Release 5.03; Siemans Analytical X-ray Instruments Inc.: Madison, Wis.).

For PXRD data herein, including Tables and Figures, each composition of the present invention may be characterized by any one, any two, any three, any four, any five, any six, any seven, any eight or more of the 2 theta angle peaks. Any one, two, three, four, five, or six DSC transitions can also be used to characterize the compositions of the present invention. The different combinations of the PXRD peaks and the DSC transitions can also be used to characterized the compositions. Single-crystal data and melting points can also be used separately, or together to characterize a composition of the present invention.

Example 1

Donepezil

ARICEPT (Donepezil Hydrochloride) is an acetylcholine esterease inhibitor used for Alzheimer disease treatment. Crystal data has been reported on a free base (unit cell) CSD, and five polymorphic HCl salts (XPD) (see EP1019374 B1).

Two polymorphs and a hydrate of donepezil free base have been obtained.

Donepezil (Free Base), Form III 20 mg donepezil HCl was dissolved in 2 mL dimethyl sulfoxide (DMSO) and 0.5 mL of 0.1 M sodium hydroxide was added. Slow evaporation at room temperature yielded thin crystalline plates. The product was identified as donepezil free base, Form III.

Crystal data for donepezil (free base), Form III: Monoclinic, $P2_1/c$; a=16.449(8) Å, b=9.355(5) Å, c=14.336(7) Å; $\beta$=112.514(10)°; V=2037.9(18) Å$^3$; Z=4

Melting Point for donepezil (free base), Form III: 74-82 degrees C.

Figure 2:
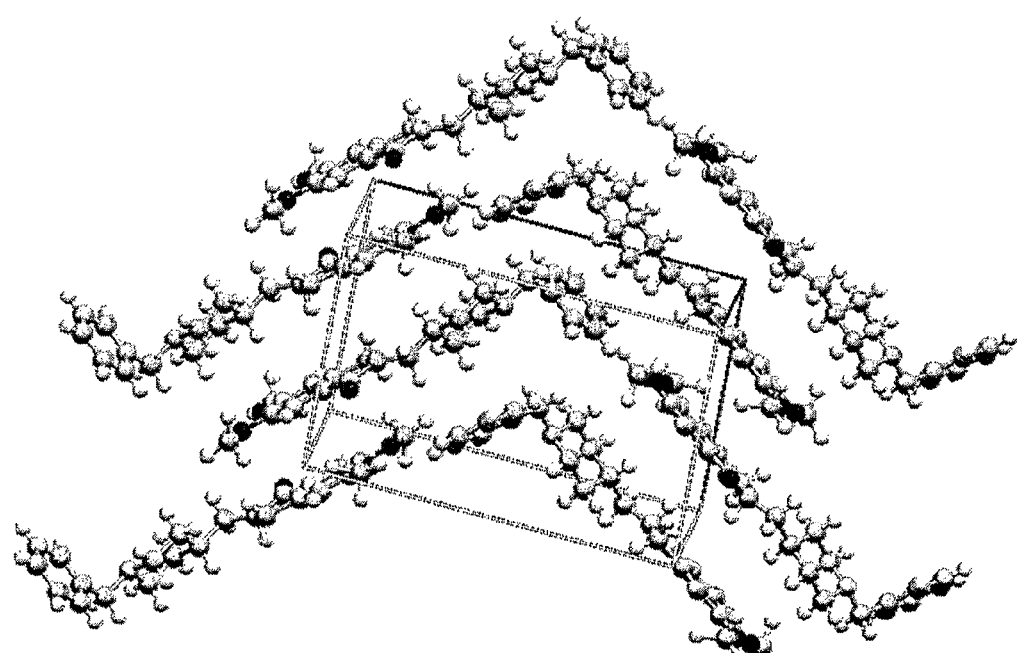
FIG. 2 shows the herring bone structure of donepezil free base, Form III

Intermolecular interactions of donepezil Form III appear to be pi stacking (FIG. 1). Donepezil Form III crystal packing appears to be in a herring bone pattern (FIG. 2).

Figure 3:
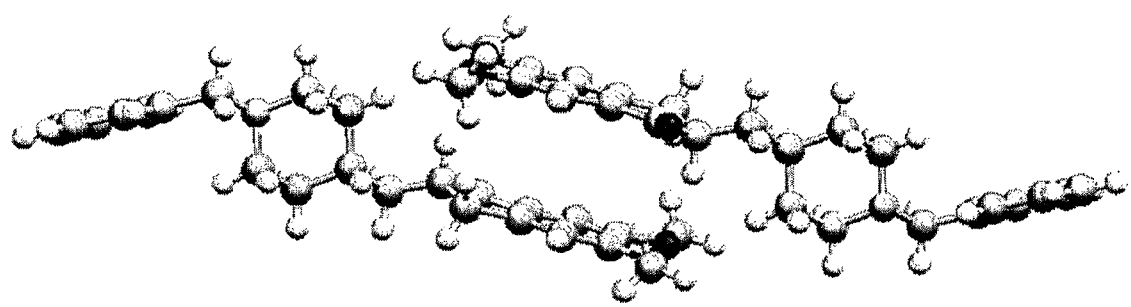
FIG. 3 shows a diagram of donepezil free base, Form IV

Donepezil (Free Base), Form IV 20 mg donepezil HCl was dissolved in 2 mL ethanol and 0.5 mL of sodium hydroxide was added. Slow evaporation at room temperature yielded oily residue. The residue was then dissolved in 1 mL methanol and 1 mL of each, acetonitrile and ethyl acetate, were added. Slow evaporation yielded a crystalline solid. The solid was determined to be donepezil free base, Form IV (FIG. 3).

Crystal data for donepezil (free base), Form IV: Monoclinic, P21/c, a=17.518(2) Å, b=10.2424(14) Å, c=11.7020(15) Å, beta=103.598(3) degrees, V=2040.8(5) Å$^3$, Z=4

Melting Point for donepezil (free base), Form IV: 76-85 degrees C.

Figure 4:
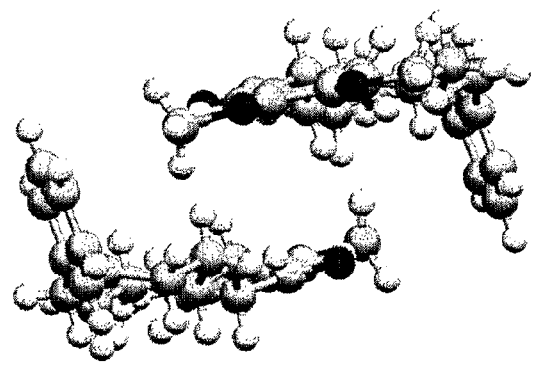
FIG. 4 shows a diagram of donepezil tetrahydrate
Figure 5:
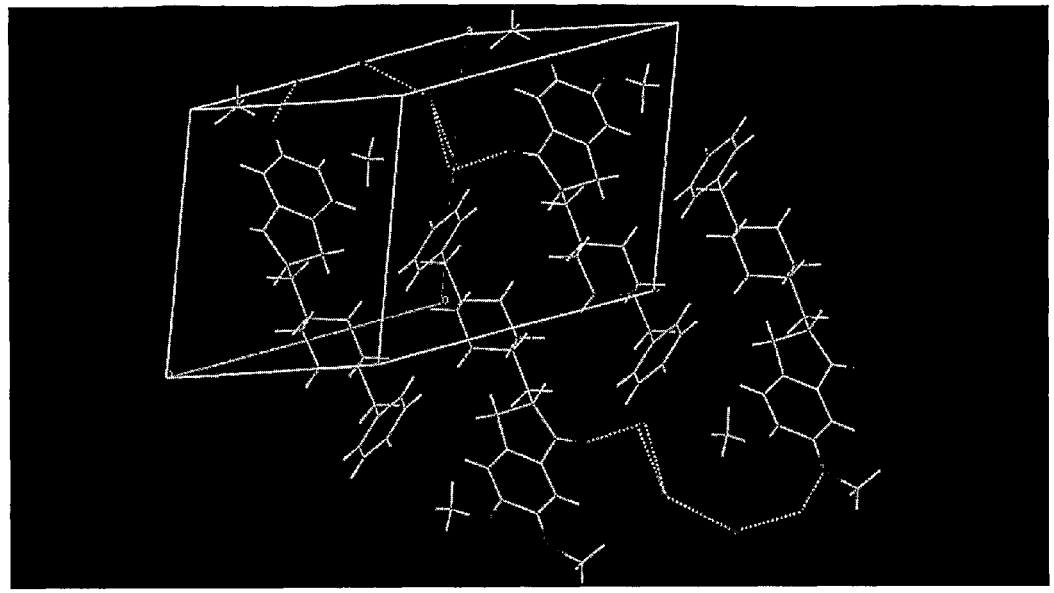
FIG. 5 shows a packing diagram of donepezil tetrahydrate

Donepezil Tetrahydrate 6 mg of donepezil and 4 mg nicotinamide were dissolved in 1 mL ethanol and an excess of water. Slow evaporation yielded thin plates of solid. The solid was determined to be donepezil tetrahydrate (FIGS. 4 and 5).

Crystal data for donepezil tetrahydrate: Triclinic, P-1, a=10.338(3) Å, b=11.319(3) Å, c=12.065(3) Å, alpha=104.335(5) degrees, beta=99.214(5) degrees, gamma=115.620(5) degrees, V=1174.2(6) Å$^3$, Z=2

Melting Point for donepezil tetrahydrate: about 86 degrees C.

Example 2

Bicalutamide

CASODEX (bicalutamide) is a non-steroidal anti-androgen used for prostate cancer treatment. It exists as racemate with anti-androgenic activity residing in the R-enantiomer and structural data has been reported in US2003191337 (incorporated herein by reference in its entirety) on one form.

5 mg Bicalutamide (racemic) was dissolved in 1 mL of chloroform. Slow evaporation at room temperature yielded colorless crystals of racemic bicalutamide, Form I.

Crystal data for Bicalutamide (racemic), Form I: Triclinic, P-1; a=7.6159(13) Å, b=11.0193(18) Å, c=11.2056(19) Å; alpha=87.301(3)°, beta=77.091(3)°, gamma=78.485(3)°; V=898.2(3) Å$^3$; Z=2

Melting point for Bicalutamide (racemic), Form I: 191-192 degrees C.

Figure 6:
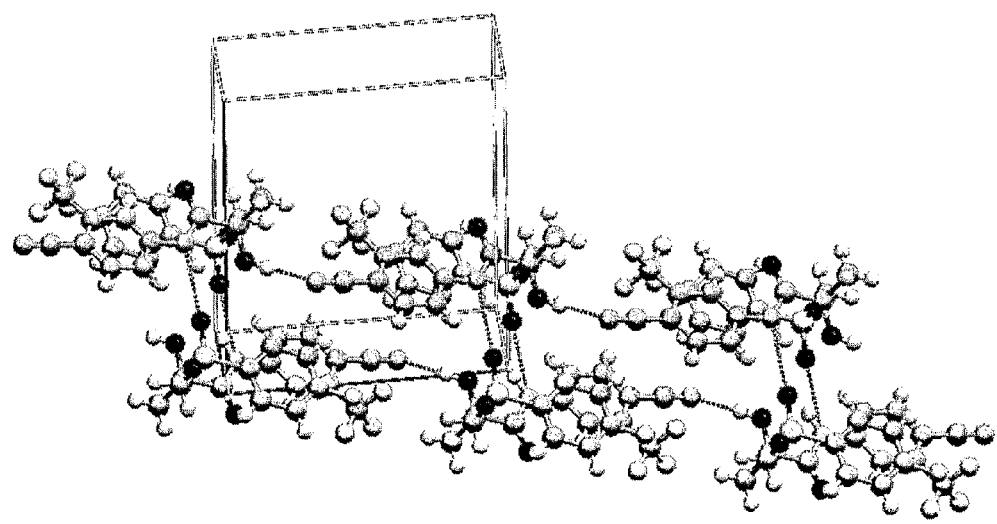
FIG. 6 shows a chain of dimers of bicalutamide
Figure 7:
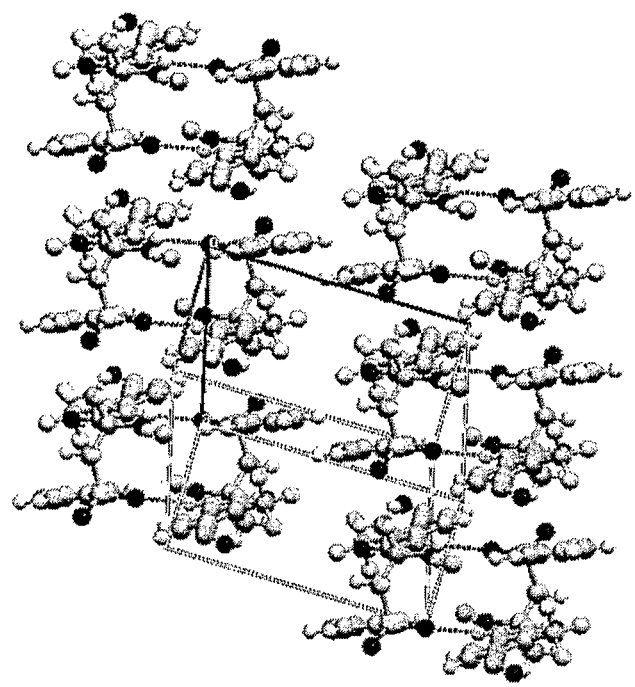
FIG. 7 shows a chain of dimers of bicalutamide (alternate view)

FIGS. 6 and 7 show a bicalutamide chain of dimers.

Example 3

Tamsulosin

Tamsulosin Hydrochloride (FLOMAX) is used in the treatment of benign prostate cancer. Structural data has been reported in Patent WO/037851 A1. Two forms of free base have also been reported (Form 1 and Form 2) and these have been characterized.

(R)-Tamsulosin HCl 11.3 mg (R)-tamsulosin HCl was dissolved in 1 mL methanol. Crystals were obtained from slow evaporation at room temperature. Crystals of the same type were also obtained on attempted co-crystallization of (R)-tamsulosin HCl (19.2 mg, 0.043 mmol) and urea (5.6 mg, 0.093 mmol) in 1 ml methanol. The crystalline form was characterized by single crystal x-ray diffraction and melting point.

Crystal Data for (R)-Tamsulosin HCl: Monoclinic, P2(1), a=7.5499(13) Å, b=9.1496(15) Å, c=31.755(5) Å, $\beta$=93.158(3)°, V=2190.2(6) Å$^3$, Z=4

Melting point for (R)-Tamsulosin HCl: 228-230 degrees C.

(R)-Tamsulosin (Free Base), Form I (R)-Tamsulosin HCl (41 mg, 0.09 mmol) was dissolved in 2 mL methanol, approximately 1 mL of 0.1 M sodium hydroxide (0.1 mmol) added. The solution was allowed to evaporate slowly for 3 days at 5 degrees C., then at room temperature. The crystalline form was characterized by single crystal x-ray diffraction and melting point.

Crystal Data for (R)-Tamsulosin (free base), Form I: Monoclinic, P2(1), a=9.4238(8) Å, b=21.4492(18) Å, c=10.4229(9) Å, $\beta$=105.776(2)°, V=2027.5(3) Å$^3$, Z=4

Melting point for (R)-Tamsulosin (free base), Form I: 120-122 degrees C.

Figure 8:
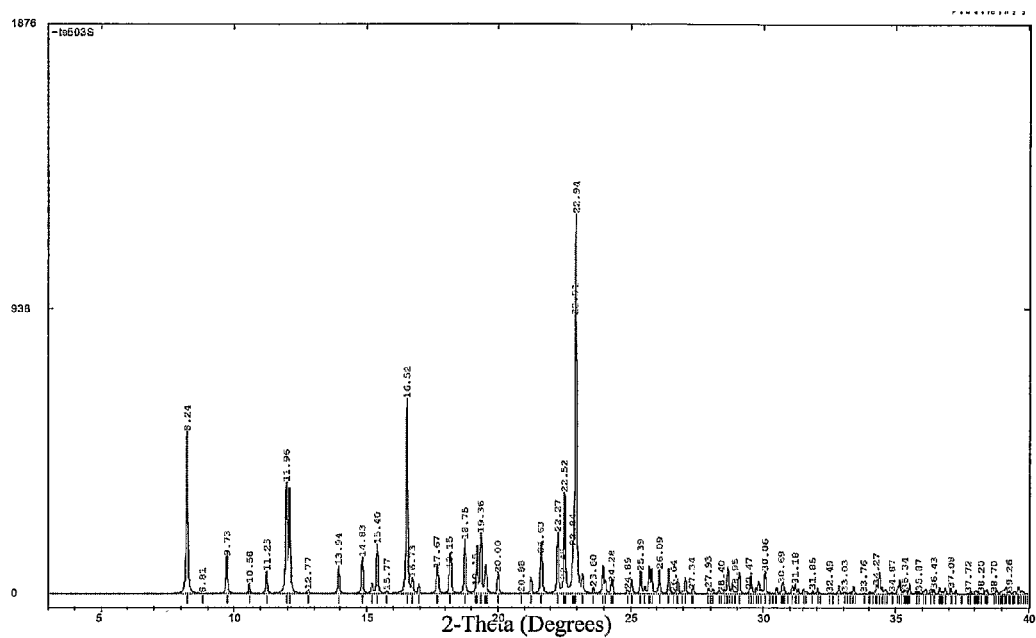
FIG. 8 shows a simulated PXRD diffractogram of tamsulosin, Form I

A simulated PXRD diffractogram is shown in FIG. 8.

(R)-Tamsulosin Hemihydrate (Free Base)

(R)-Tamsulosin (free base) Form 1 (8.2 mg, 0.02 mmol) and urea (4 mg, 0.07 mmol) in 1 mL methanol, yielded crystal of (R)-Tamsulosin hemihydrate upon slow evaporation of the solvent at room temperature. The crystalline form was characterized by single crystal x-ray diffraction and melting point.

Crystal Data for (R)-Tamsulosin Hemihydrate: Monoclinic, C2, a=15.7563(17) Å, b=11.8043(12) Å, c=21.978(2) Å, β=99.1016(2)°, V=4037.3(7) Å$^3$, Z=8

Melting point for (R)-Tamsulosin Hemihydrate: 104-108 degrees C.

Figure 9:
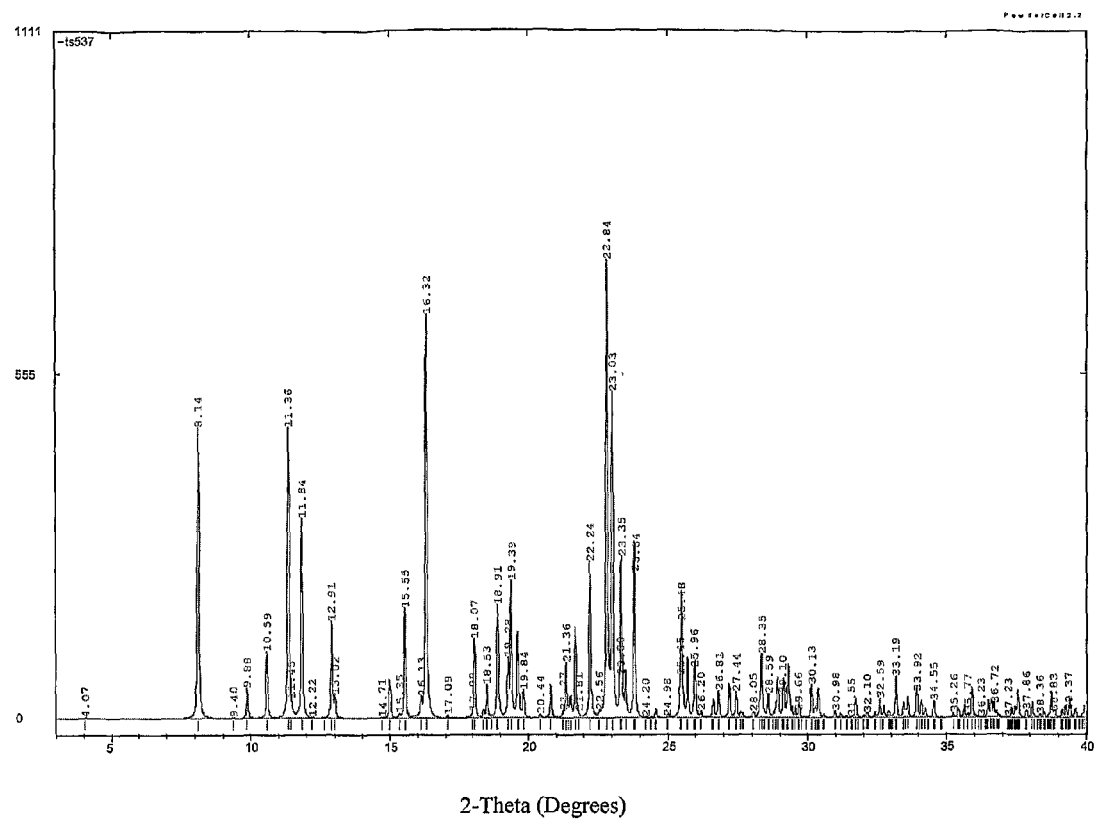
FIG. 9 shows a simulated PXRD diffractogram of tamsulosin hemihydrate

A simulated PXRD diffractogram is shown in FIG. 9. (R)-Tamsulosin hemihydrate exhibits a similar, but not identical powder pattern to Form 1 of WO/037851 A1.

(R)-Tamsulosin (Free Base), Form II 14.2 mg (R)-Tamsulosin HCl was dissolved in 0.5 mL ethylenediamine. Crystals were obtained from slow evaporation of the solvent, at room temperature.

Crystal Data for (R)-Tamsulosin (free base), Form II: Monoclinic, C2, a=20.490(4) Å, b=13.028(2) Å, c=15.664(3) Å, β=103.846(3)°, V=4059.9(12) Å$^3$, Z=8

Melting point for (R)-Tamsulosin (free base), Form II: 109-113 degrees C.

Figure 10:
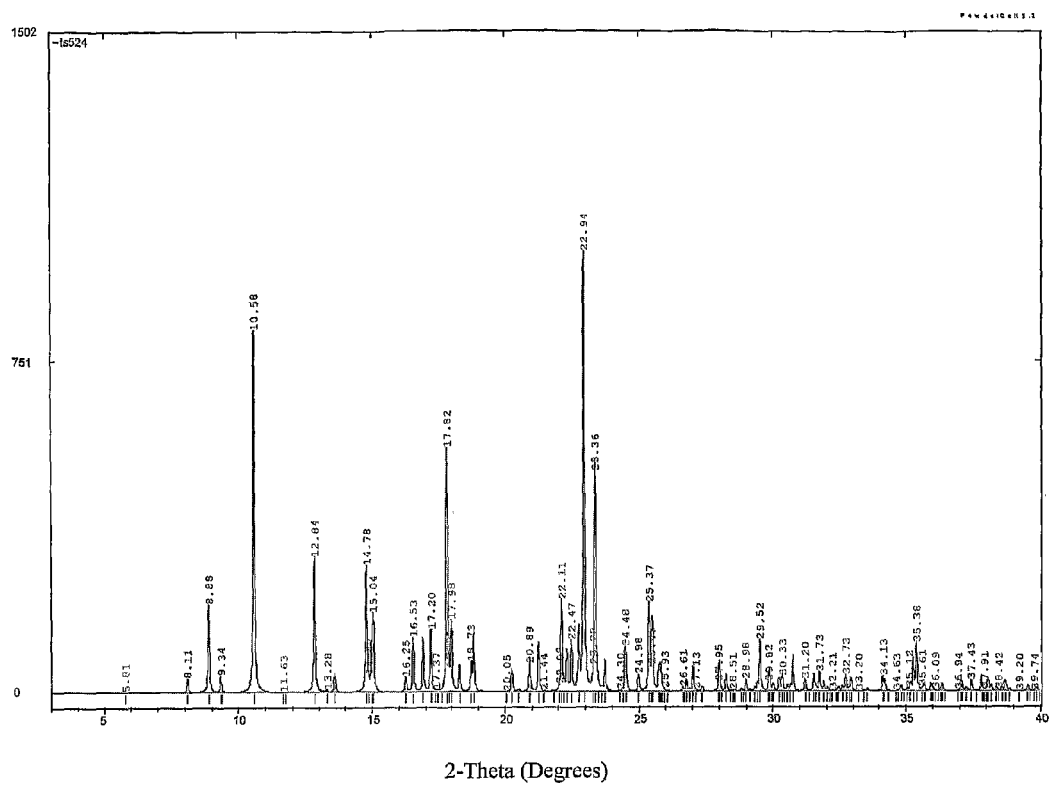
FIG. 10 shows a simulated PXRD diffractogram of tamsulosin, Form II

A simulated PXRD diffractogram is shown in FIG. 10.

Example 4

Viracept

VIRACEPT (Nelfinavir Mesylate) is a selective, competitive, reversible inhibitor of HIV protease which shows a strong food effect.

An HCl salt of nelfinavir was obtained via the following procedure. An equimolar ratio of nelfinavir mesylate and thiamine HCl in propylene glycol were mixed, heated to dissolution and slowly evaporated (over 2 months). Crystals formed as tiny needles, clear in color.

Crystal Data for Nelfinavir HCl: Orthorhombic, P212121, a=10.7998(11) Å, b=10.9951(11) Å, c=26.198(3) Å, alpha=90 degrees, beta=90 degrees, gamma=90 degrees, V=3110.9(5) Å$^3$, Z=4.

Figure 11:
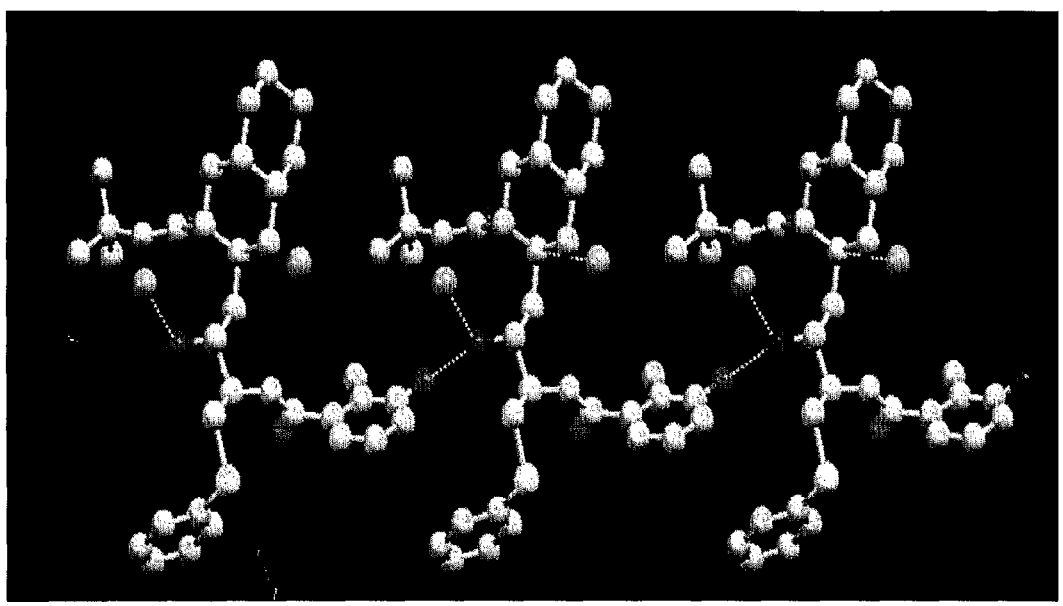
FIG. 11 shows the OH—OH chain of nelfinavir HCl salt
Figure 12:
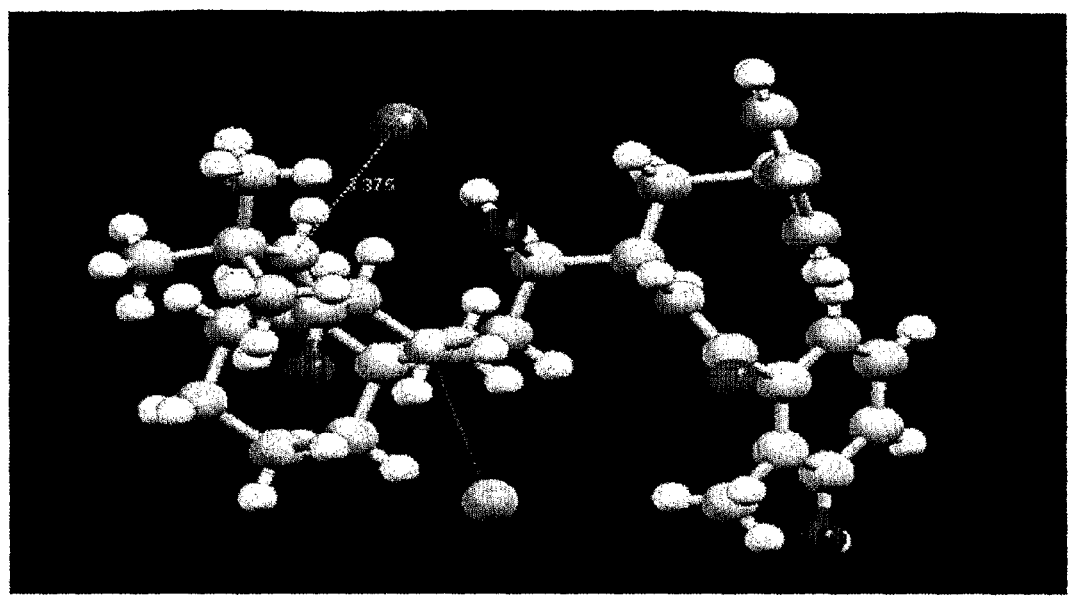
FIG. 12 shows the chloride interaction of nelfinavir HCl salt
Figure 13:
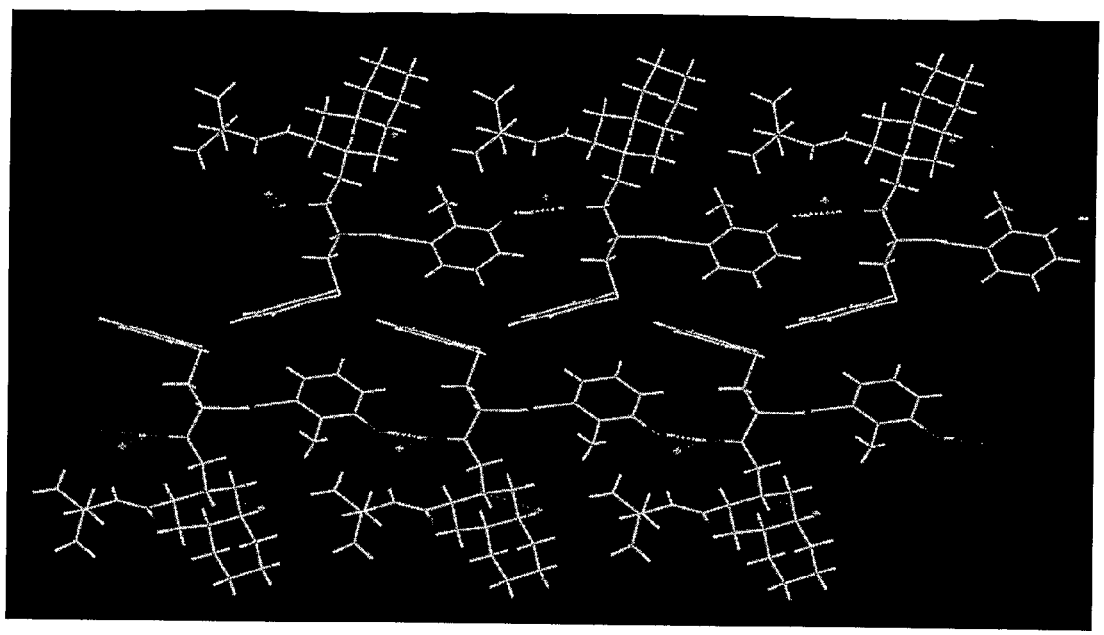
FIG. 13 shows the packing diagram of nelfinavir HCl salt

FIGS. 11-13 shows the OH—OH chain, the chloride interaction, and the packing diagram of nelfinavir HCl, respectively.

Example 5

Anastrozole

Anastrozole is an aromatase inhibitor used for breast cancer treatment (see U.S. Pat. No. 4,935,437).

Figure 14:
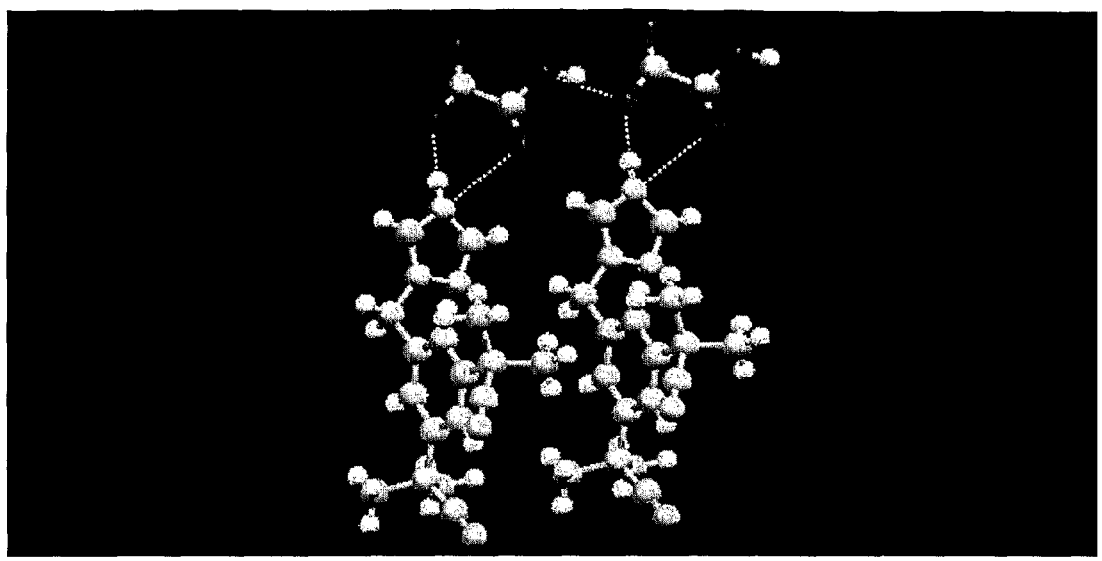
FIG. 14 shows the ionic interaction between protonated anastrozole and the oxalate anion
Figure 15:
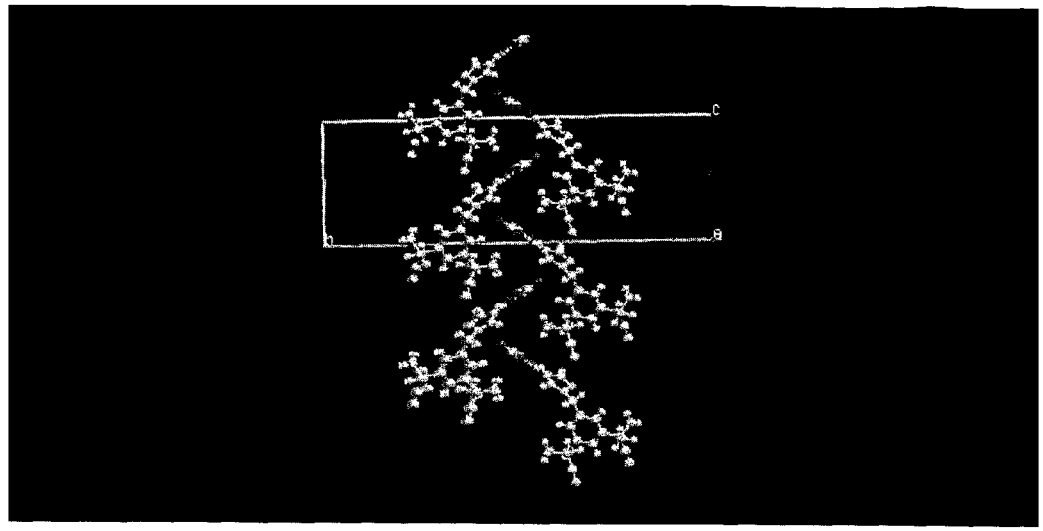
FIG. 15 shows a packing diagram of anastrozole oxalate salt

Anastrozole (28.3 mg, 0.096 mmol) and oxalic acid (8.9 mg, 0.099 mmol) were dissolved in 1 mL methanol:acetonitrile (1:1 v/v) solution. Crystals of anastrozole oxalate were obtained from slow evaporation at room temperature in an ambient atmosphere. Crystals of anastrozole oxalate were also obtained via crystallization of anastrozole (38.3 mg, 0.131 mmol) and oxalic acid (10.7 mg, 0.119 mmol) in 1.5 mL methanol:ethyl acetate (1:0.5 v/v) solution. The crystalline form of anastrozole oxalate was characterized by single crystal x-ray diffraction and melting point. (See FIGS. 14 and 15)

Crystal Data for anastrozole oxalate: Monoclinic, Cc, a=5.6514(8) Å, b=32.718(5) Å, c=10.7384(17) Å, alpha=90 degrees, beta=101.652(4) degrees, gamma=90 degrees, V=1944.7(5) Å$^3$, Z=4.

Melting point for anastrozole oxalate: 164-166 degrees C.

Example 6

Polymorph of 5-Fluorouracil

To 5-fluorouracil (1 g, 7.69 mmol) and nicotinamide (0.94 g, 7.69 mmol) was added methanol (100 mL). The solution was heated at 65 degrees C. and sonicated until all the material dissolved. The solution was then cooled to 5 degrees C. and maintained at that temperature overnight. After about 3 days a white precipitate was observed and collected. The precipitate was analyzed by TGA, DSC, and PXRD and determined to be a polymorph of 5-fluorouracil.

Figure 16:
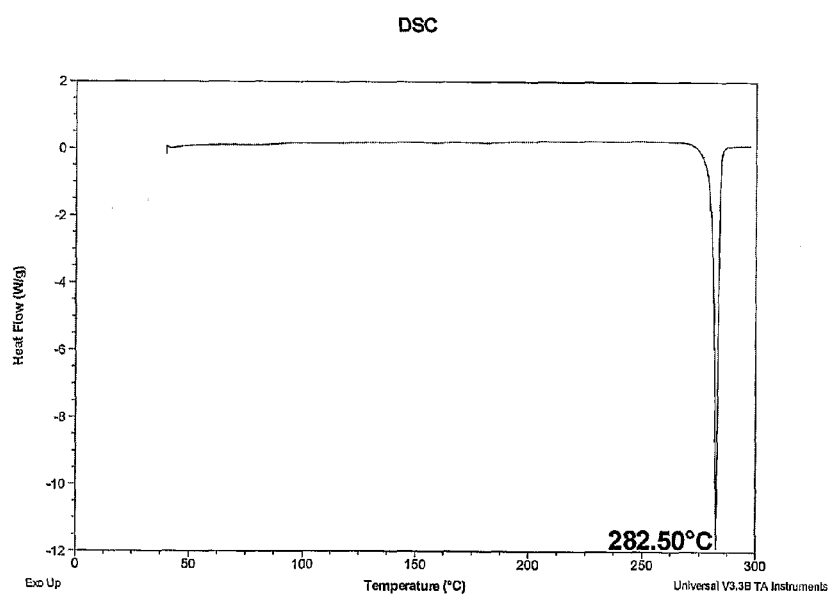
FIG. 16 shows a TGA thermogram of a 5-fluorouracil polymorph
Figure 17:
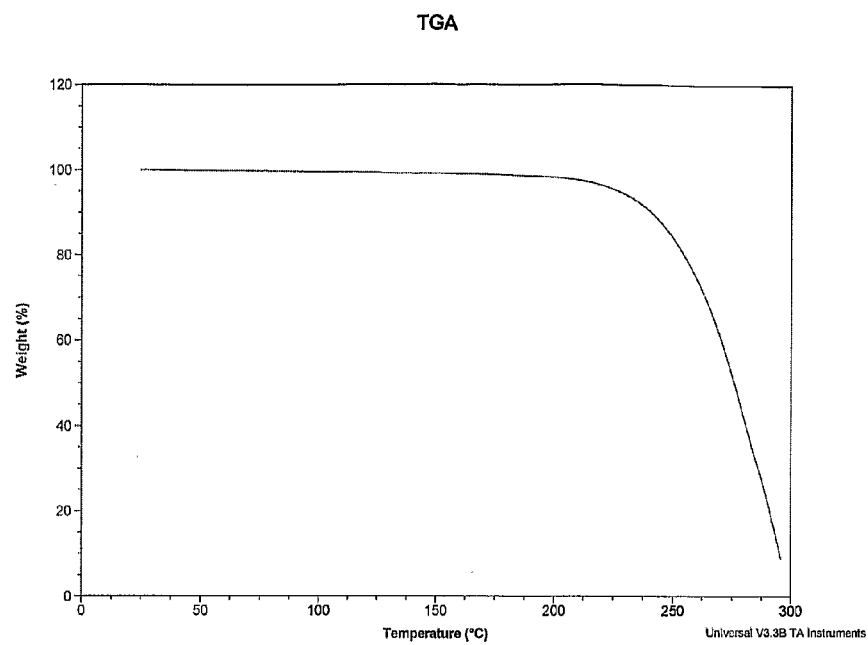
FIG. 17 shows a DSC thermogram of a 5-fluorouracil polymorph
Figure 18:
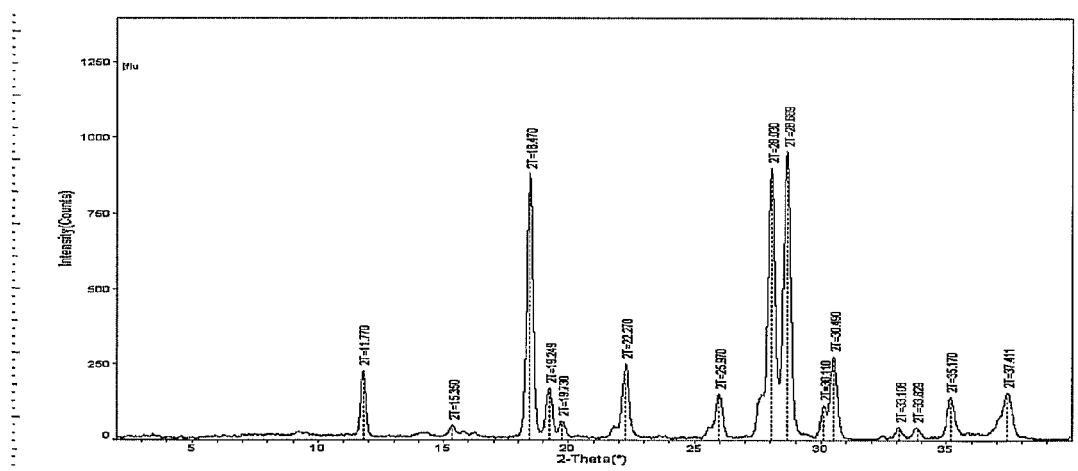
FIG. 18 shows a PXRD diffractogram of a 5-fluorouracil polymorph

The DSC thermogram showed an endothermic transition at about 282.5 degrees C. (See FIG. 16). The TGA thermogram showed weight loss beginning at about 200 degrees C. (See FIG. 17). The 5-fluorouracil polymorph can also be characterized by any one, any two, any three, any four, any five, or any six or more of the peaks in the PXRD diffractogram in FIG. 18 including, but not limited to, 11.77, 18.47, 22.27, 25.97, 28.03, 28.67, 30.49, 35.17, and 37.41 degrees 2-theta.

Example 7

Hydrate of Celecoxib Sodium Salt

Figure 19:
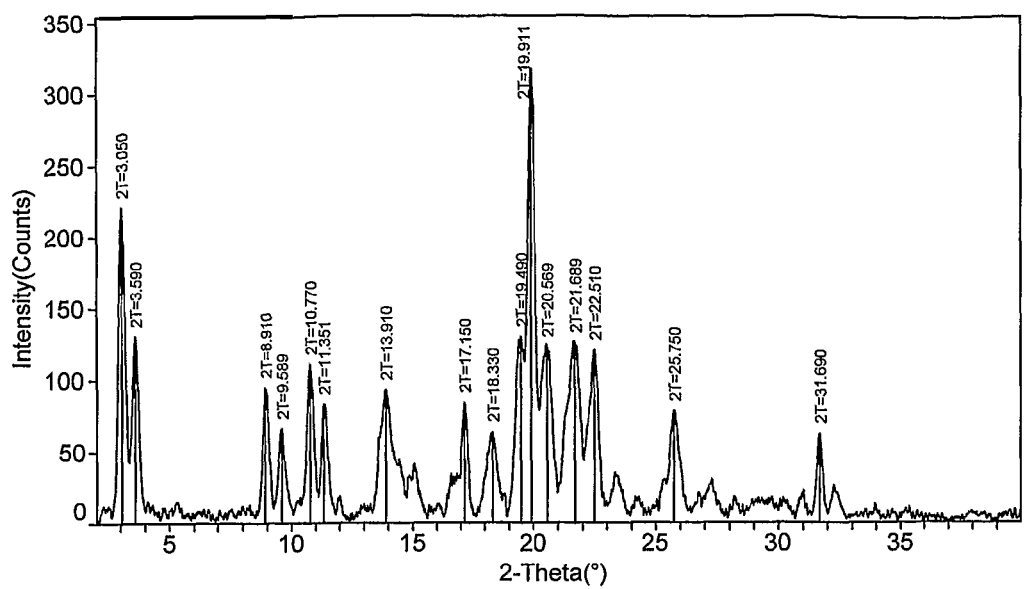
FIG. 19 shows a PXRD diffractogram of a hydrate of celecoxib sodium salt

The preparation and characterization of celecoxib sodium salt is described in International Applications WO04/000284 and WO04/061433. A hydrate form of celecoxib sodium salt was prepared by placing a sample of celecoxib sodium salt in a controlled humidity environment at 50-75% RH (percent relative humidity) and room temperature (about 22 to 25 degrees C.) for 1-24 hours. The sample was protected from exposure to $CO_2$ gas. The hydrate form remained as long as humidity was controlled and no $CO_2$ was admitted to the storage vessel. The celecoxib sodium salt hydrate can be characterized by any one, any two, any three, any four, any five, or any six or more of the peaks in the PXRD diffractogram in FIG. 19 including, but not limited to, 3.05, 3.59, 8.91, 9.59, 10.77, 11.35, 13.91, 17.15, 18.33, 19.49, 19.91, 20.57, 21.69, 22.51, 25.75, and 31.69 degrees 2-theta.

Example 8

Fluconazole Benzene Solvate

To fluconazole (18 mg, 0.06 mole) was added oleic acid (30 mg, 0.11 mole) and dissolved over low heat with 1 mL benzene. Crystals appeared after 6 days using slow evaporation. The crystals were analyzed by IR (infrared spectroscopy) and single-crystal x-ray analysis.

Figure 20:
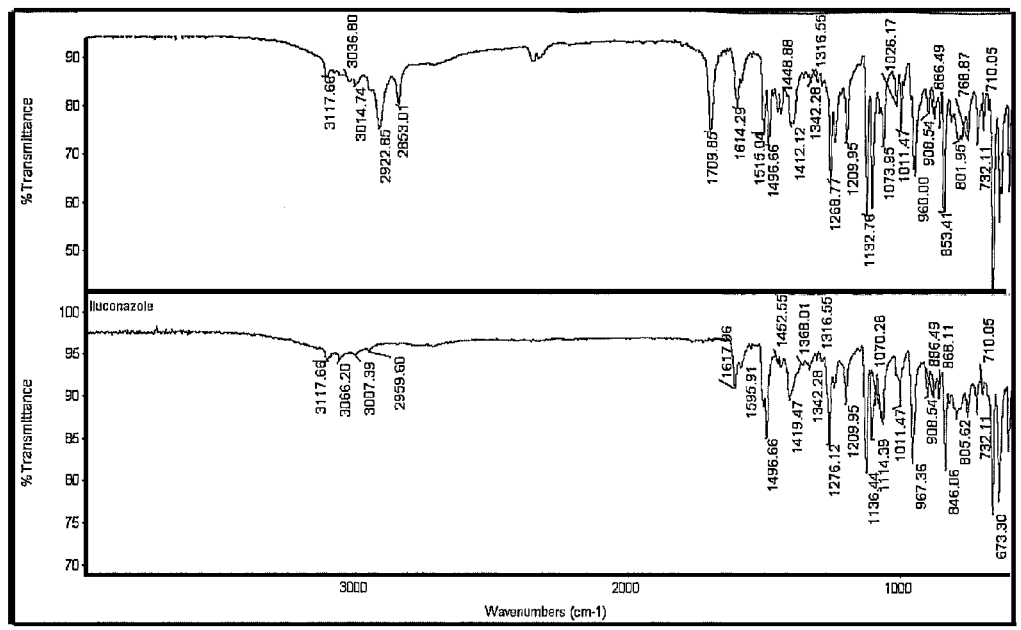
FIG. 20 shows an IR spectrum of a fluconazole benzene solvate (top spectrum)

IR data was acquired using a Nicolet Avatar 320 FTIR instrument. IR data are shown in FIG. 20, which includes IR spectra of the fluconazole benzene solvate (top) and fluconazole (bottom). The fluconazole benzene solvate can be characterized by any one, any two, any three, any four, any five, or any six or more of the peaks in the IR (top) spectrum in FIG. 20 including, but not limited to, 2923, 1710, 1614, 1515, 1497, 1412, 1269, 1210, 1133, 960, 853, or 732 cm$^{-1}$.

Crystal Data for fluconazole benzene solvate: Orthorhombic, Pba2, a=12.9209(10) Å, b=38.512(3) Å, c=5.9759(4) Å, alpha=90 degrees, beta=90 degrees, gamma=90 degrees, V=2973.6(4) Å$^3$, Z=8.

Figure 21:
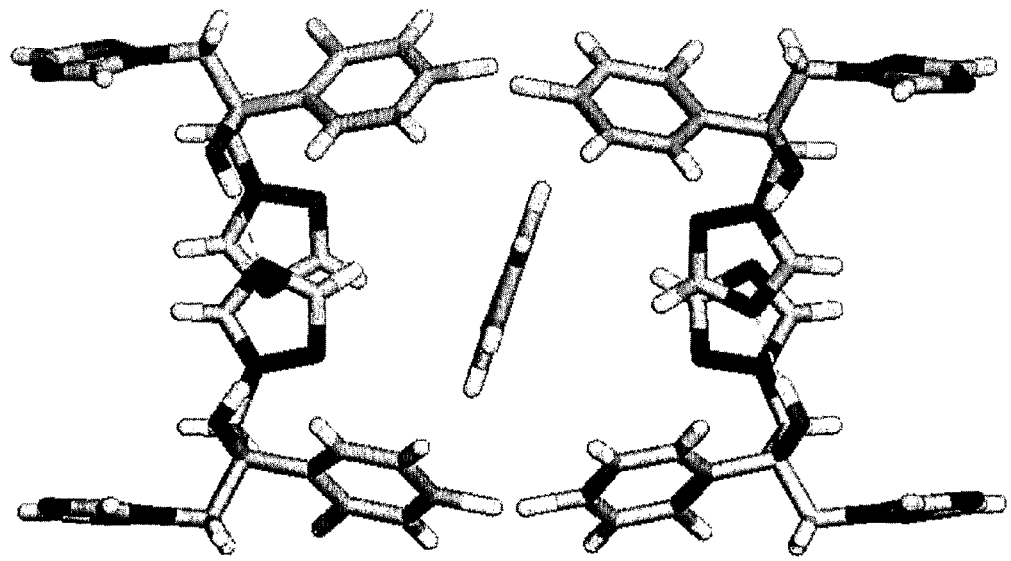
FIG. 21 shows a packing diagram of a fluconazole benzene solvate

FIG. 21 shows a packing diagram of the fluconazole benzene solvate.

Example 9

Mirtazapine Hydrate

Mirtazapine was extracted from tablets of Remeron® using methylene chloride. Slow evaporation of the solvent yielded the mirtazapine hydrate.

Crystal Data for mirtazapine hydrate: Monoclinic, P2(1)/c, a=9.783(3) Å, b=17.267(5) Å, c=8.886(3) Å, alpha=90 degrees, beta=106.340(7) degrees, gamma=90 degrees, V=1440.4(8) Å$^3$, Z=4.

Example 10

1:1:1 Lansoprazole:Isopropanol:Water Complex 20 mg of lansoprazole and 6 mg of TRIS (tris[hydroxymethyl]aminomethane) were dissolved in 4 mL of isopropanol. Slow evaporation yielded colorless needles after 15 days. The solid was analyzed by IR and single-crystal x-ray analysis. The solid was determined to be a 1:1:1 lansoprazole:isopropanol:water complex.

Figure 22:
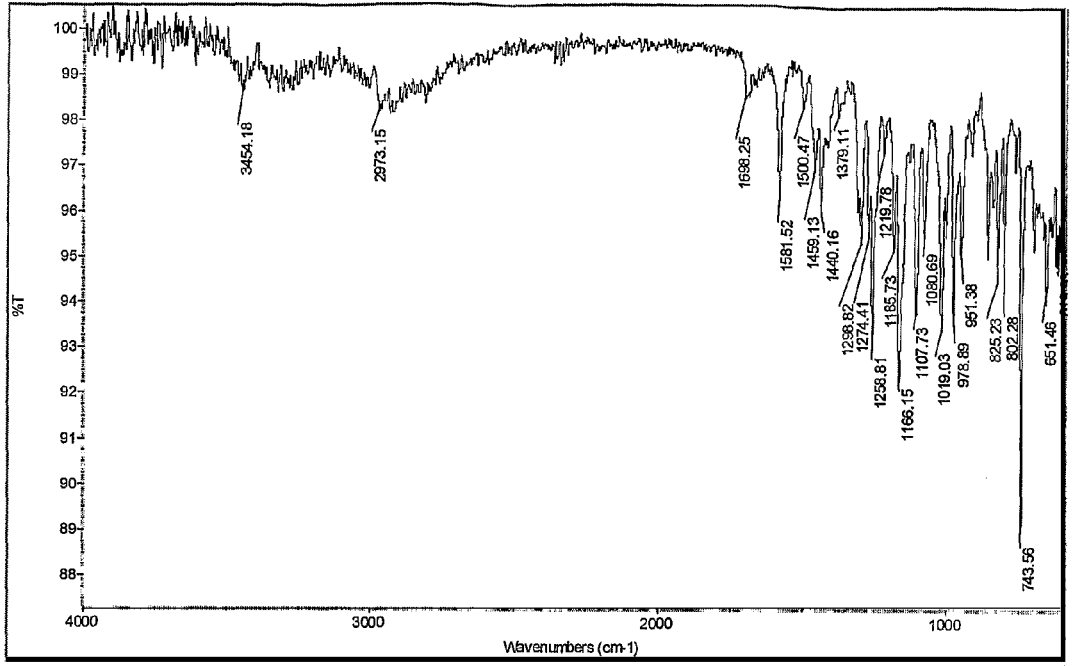
FIG. 22 shows an IR spectrum of lansoprazole isopropanol hydrate

IR data was acquired using a Nicolet Avatar 320 FTIR instrument. IR data of the lansoprazole:isopropanol:water complex are shown in FIG. 22. The lansoprazole:isopropanol:water complex can be characterized by any one, any two, any three, any four, any five, or any six or more of the peaks in the IR spectrum in FIG. 22 including, but not limited to, 1698, 1582, 1299, 1259, 1166, 1108, 1019, 979, 951, and 744 cm$^{-1}$.

Crystal Data for lansoprazole:isopropanol:water complex: Orthorhombic, Pbca, a=5.5256(11) Å, b=25.310(5) Å, c=29.560(6) Å, alpha=90 degrees, beta=90 degrees, gamma=90 degrees, V=4134.0(15) Å$^3$, Z=8.

Figure 23:
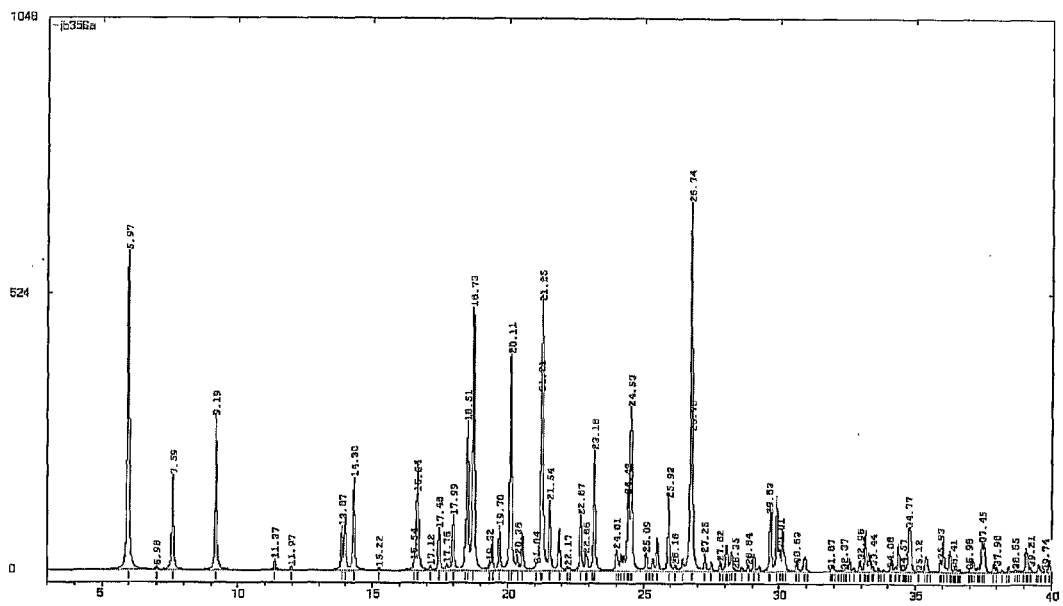
FIG. 23 shows a simulated PXRD diffractogram of lansoprazole isopropanol hydrate
Figure 24:
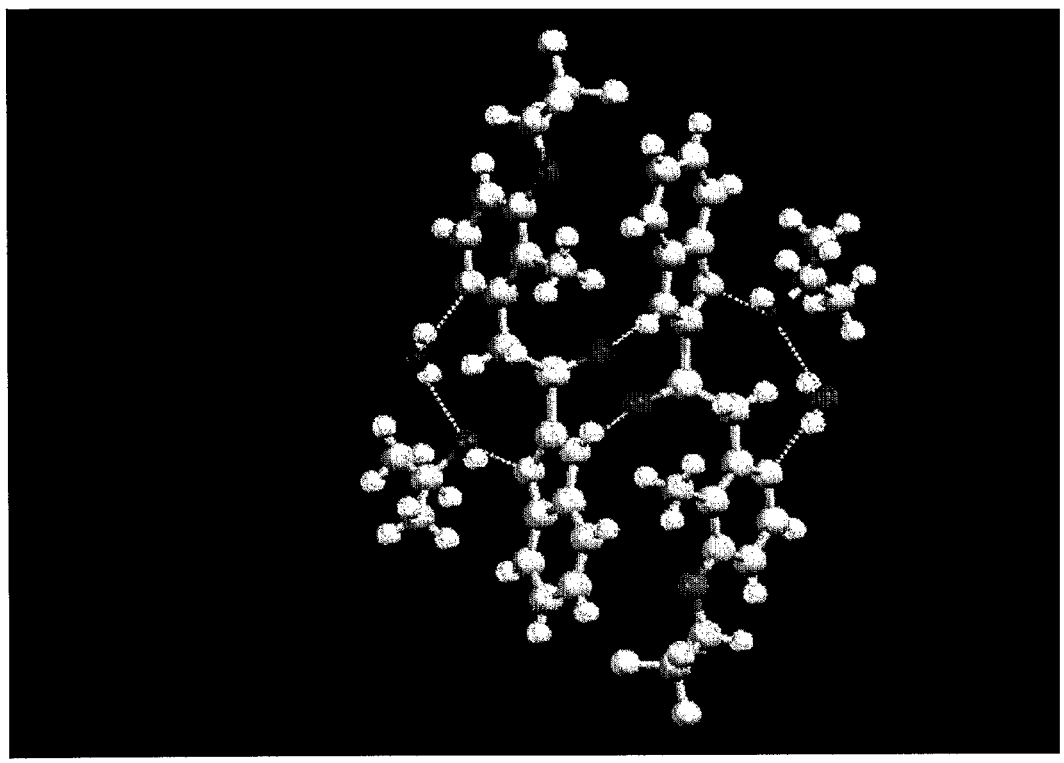
FIG. 24 shows a packing diagram of a lansoprazole:isopropanol:water complex

FIG. 23 shows a simulated PXRD diffractogram constructed from the single-crystal x-ray data. FIG. 24 shows a packing diagram for the lansoprazole:isopropanol:water complex.

What is claimed is:

1. Anastrozole oxalate, wherein said anastrozole oxalate exhibits the following crystal parameters: a=5.6514(8) Å, b=32.718(5) Å, c=10.7384(17) Å, and beta=101.652(4) degrees.

2. The anastrozole oxalate of claim 1, wherein said anastrozole oxalate is crystalline.

3. The anastrozole oxalate of claim 1, wherein said anastrozole oxalate exhibits a monoclinic crystal system.

4. The anastrozole oxalate of claim 1, wherein said anastrozole oxalate exhibits a Cc space group.

5. The anastrozole oxalate of claim 1, wherein said anastrozole oxalate is characterized by a melting point at about 164-166 degrees C.

6. A pharmaceutical dosage form comprising a therapeutically effective amount of anastrozole oxalate according to claim 1.

7. A method for treating a subject with breast cancer, comprising administering to said subject a therapeutically effective amount of anastrozole oxalate according to claim 1.

* * * * *

UNITED STATES PATENT AND TRADEMARK OFFICE
CERTIFICATE OF CORRECTION

PATENT NO. : 8,436,029 B2
APPLICATION NO. : 10/599010
DATED : May 7, 2013
INVENTOR(S) : Hickey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1996 days.

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,436,029 B2  Page 1 of 1
APPLICATION NO. : 10/599010
DATED : May 7, 2013
INVENTOR(S) : Magali Bourghol Hickey et al.

It is certified that error appears in the above-identified patent and that said Letters Patent is hereby corrected as shown below:

In the Specification

Column 8,
Lines 59-60, "(e.g., Cerelose$^{TM}$)" should read --(e.g., Cerelose$^{TM}$ 2000)--.

Signed and Sealed this
Sixth Day of May, 2014

Michelle K. Lee
*Deputy Director of the United States Patent and Trademark Office*